US012303712B1

(12) United States Patent
Finger et al.

(10) Patent No.: US 12,303,712 B1
(45) Date of Patent: May 20, 2025

(54) CONFORMAL SYSTEM FOR THERAPEUTIC BETA OR LOW-ENERGY GAMMA RADIATION SHIELDING

(71) Applicant: IP LIBERTY VISION CORPORATION

(72) Inventors: Paul T. Finger, New York, NY (US); Toby Welles, New York, NY (US)

(73) Assignee: IP LIBERTY VISION CORPORATION, New York, NY (US)

( * ) Notice: Subject to any disclaimer, the term of this patent is extended or adjusted under 35 U.S.C. 154(b) by 0 days.

(21) Appl. No.: 18/437,442

(22) Filed: Feb. 9, 2024

Related U.S. Application Data

(60) Provisional application No. 63/484,496, filed on Feb. 11, 2023.

(51) Int. Cl.

| | |
|---|---|
| ***A61N 5/10*** | (2006.01) |
| ***G21F 5/015*** | (2006.01) |

(52) U.S. Cl.
CPC .......... *A61N 5/1028* (2013.01); *G21F 5/015* (2013.01); *A61N 2005/1089* (2013.01); *A61N 2005/1094* (2013.01)

(58) Field of Classification Search
CPC .......... A61N 5/1028; A61N 2005/1089; A61N 2005/1094; G21F 5/015
See application file for complete search history.

(56) References Cited

U.S. PATENT DOCUMENTS

| | | | | |
|---|---|---|---|---|
| 5,548,125 | A | 8/1996 | Sandbank | |
| 5,638,545 | A | 6/1997 | Rosner | |
| 6,310,355 | B1 | 10/2001 | Cadwalader | |
| 6,749,859 | B2 | 6/2004 | Leibowitz | |
| 2004/0092892 | A1* | 5/2004 | Kagan | A61B 17/0401 604/270 |
| 2006/0060718 | A1 | 3/2006 | Bigelow | |
| 2014/0257013 | A1* | 9/2014 | D'Andrea | A61N 5/1071 600/2 |
| 2016/0361565 | A1 | 12/2016 | Fukumoto et al. | |
| 2018/0296855 | A1* | 10/2018 | Lohrenz | A61N 5/1017 |

FOREIGN PATENT DOCUMENTS

| | | |
|---|---|---|
| GB | 1420940 | 1/1976 |

* cited by examiner

*Primary Examiner* — Carrie R Dorna
*Assistant Examiner* — Joshua Darly D Lannu
(74) *Attorney, Agent, or Firm* — Smith Tempel; Steven P. Wigmore

(57) ABSTRACT

A conformal system and method for radiation shielding may include a container made of a first material that defines a closed volume. The closed volume may provide a seal for a shielding filler material. The shielding filler material may be provided within the closed volume defined by the container. The shielding filler material may include a second material different from the first material. Both the first and second materials may provide shielding against beta particle or low energy gamma radiation. The container may define an aperture such that an object may pass through the aperture, while the closed volume maintains its seal for the shielding filler material. The container may be used with surgical procedures where radiation is emitted as a treatment for living tissue.

20 Claims, 13 Drawing Sheets

General Cross Sectional Views of Typical Shielding Bag
(all dimensions and shapes approximate)

View A-A (alt. embodiment see fig.1)

View A-A (alt. embodiment see fig.6)

View B-B (alt. embodiment see fig.6)

lateral radiation
101
800
105
102
1100
source
tissue
idealized
shield
(half shown)
10mm
Minimum

CONFORMAL SYSTEM FOR THERAPEUTIC BETA OR LOW-ENERGY GAMMA RADIATION SHIELDING

FIELD OF INVENTION

A conformal shield is described to provide shielding against most beta or low-energy gamma radiation emissions in areas not targeted for treatment, including adjacent patient tissues and personnel in the vicinity.

BACKGROUND

In brachytherapy treatment of the eye using beta radiation from sources such as strontium 90, yttrium 90, phosphorus 32 or ruthenium/rhodium 106, or using low-energy gamma radiation from sources such as iodine-125, palladium-103, or cesium-131, it is common to place a partly shielded radiation source on the affected tissue. Brachytherapy applicators have been devised to be directional, however with modern usage, treatments can be associated with an escape of unwanted lateral radiation, (e.g., backscatter, the photoelectric effect, and miss-application) sometimes directed towards the patient and operating room personnel.

Since healthcare workers perform repeated procedures, it is important to reduce any potential extraneous radiation emitted from radiation sources. Accordingly, there is a need in the art to provide a radiation shield that can be held in place adjacent to a radiation source, while not interfering with a radiation treatment medical procedure.

There is also need in the art for a radiation shield that conforms to variable anatomical contours of the body and may be uniquely shaped and/or naturally conformal to a patient's individual anatomy. There is a further need in the art for a such a radiation shield which may be sterilizable for use in the operating room, is cost-effective to manufacture, and that generally presents no risk to the patient.

SUMMARY OF THE INVENTION

A radiation shielding system and method usually satisfies at least three requirements: the method and system may provide adequate/sufficient shielding, the method and system may conform to variable anatomic contours around the eye, and the method and system may be applied in position (during brachytherapy) without interference with surgical activities. The description that follows addresses each of these aspects.

A conformal system and method for radiation shielding may include a container made of a first material that defines a volume. The volume may have a seal for containing a shielding filler material. The shielding filler material may be provided within the volume defined by the container. The shielding filler material may comprise a second material different from the first material.

Both the first and second materials may provide shielding against beta particle or low energy gamma radiation. The container may define an aperture such that an object may pass through the aperture, while the container maintains its seal for the shielding filler material. The container may be used with surgical procedures where radiation is emitted as treatment for human tissue.

The container may further comprise at least one tab and a hole for receiving a fastener. The first material may comprise at least one of: a solid material that is a flexible and tear-resistant, and a material suitable for contact with human skin.

The second material may comprise at least one of: a liquid or gel. The second material may comprise at least one of: water, carbomer, carbopol, xanthan gum and gelatin, gelatinous materials including a silicone and an alginate, and flexible or semi-rigid, or moldable firmer compounds such as alginates, silicones, putties, epoxy materials, or supersaturated crystal-forming liquids.

According to another exemplary aspect, a conformal system and method for radiation shielding may include a container made of a first material that defines a volume. The volume may provide a seal for containing a shielding filler material and the container may have, generally, a toroidal geometry. The shielding filler material may be positioned within the volume defined by the container. The shielding filler material may comprise a second material different from the first material.

Both the first and second materials may provide shielding against beta particle or low energy gamma radiation. And the container may further comprise an aperture through the toroidal geometry such that an object may pass through the aperture, while the container maintains its seal for the shielding filler material.

This summary is provided to introduce a selection of concepts that are further described below in the detailed description. This summary is not intended to identify key or essential features of the claimed subject matter, nor is it intended to be used as an aid in limiting the scope of the claimed subject matter.

BRIEF DESCRIPTION OF THE DRAWINGS

In the Figures, like reference numerals refer to like parts throughout the various views unless otherwise indicated. For reference numerals with letter character designations such as "102A" or "102B", the letter character designations may differentiate two like parts or elements present in the same Figure. Letter character designations for reference numerals may be omitted when it is intended that a reference numeral to encompass all parts having the same reference numeral in all Figures.

DETAILED DESCRIPTION OF EXEMPLARY EMBODIMENTS

Figure 1A:
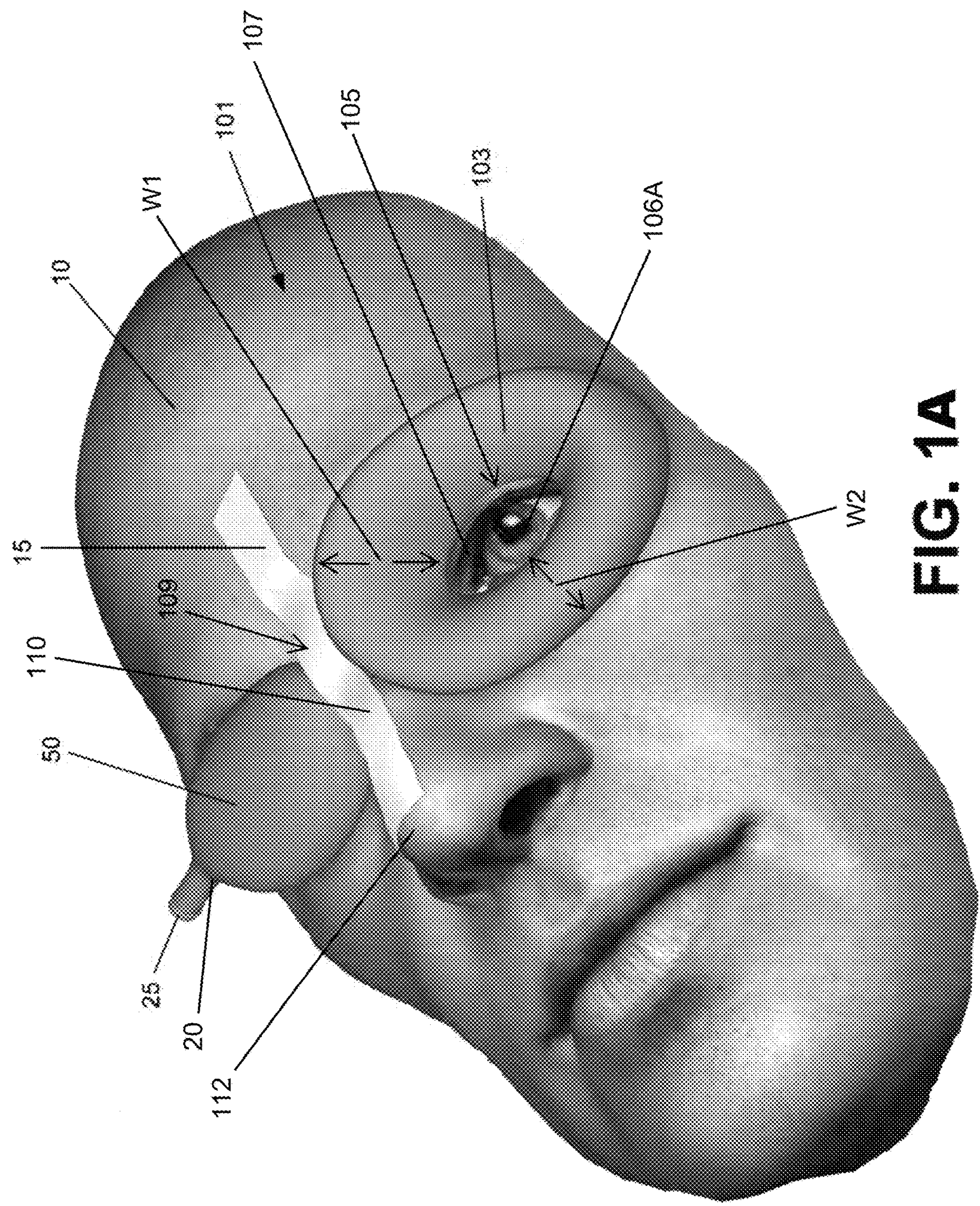
FIG. 1A illustrates an exemplary embodiment of a shield bag system that has two lobes that are coupled together.

The word "exemplary" is used herein to mean "serving as an example, instance, or illustration." Any aspect described herein as "exemplary" is not necessarily to be construed as preferred or advantageous over other aspects.

Beta-particle shielding proximate to the radiation source is best achieved with low-density materials. In the case of beta radiation, such low-density materials do not abruptly reduce the particles' velocity, and generally do not create significant amounts of unwanted and potentially hazardous bremsstrahlung x-rays. In contrast, high-density materials, such as, but not limited to, metals, which abruptly reduce the velocity of particles and produce significant quantities of these unwanted bremsstrahlung x-ray emissions.

In the case of gamma radiation, a greater thickness or high-atomic-number "high Z" component shielding material is needed to achieve the same shielding effect due to the fact that gamma radiation is similar to x-rays, such radiation consisting of photons. The dimensions of, and materials for the shielding described herein are suitable for beta sources.

In contrast, if utilizing low density materials, the shielding required by gamma sources would have to be several times thicker, which can be achieved albeit with shield configurations better suited to less dimensionally constrained, non-ophthalmic treatment sites. Or, higher-density shielding materials could be substituted for those described herein to shield beta-radiation, such as barium suspensions, ferrofluids, or metal-filled gels, putties or pastes in order to maintain the required thicknesses of shielding in a range similar to those described herein for beta sources.

With present medical procedures, a source of radiation may be introduced within an applicator and placed against the surface of the eye. While the radiation from the sides of the source directed away from and peripheral to the treatment site can be shielded by the holder, typically side-scatter radiation may escape from beneath the interface between the eye surface and the source.

This may be due to the fact that the eye surface is rounded, that the practitioner may not hold the source perfectly flush against the eyeball, or during transit and during placement and removal of the source from the scleral surface. Thus, the supplemental surrounding shielding element (SSSE) described herein, was created to be a useful additional safety measure against scattered radiation from a radiation source.

In order to create the SSSE for ocular use, the device needs to be conformed to the patient's facial contours and the site of the procedure. This is accomplished by utilizing a flexible or malleable substance that can be contained within an elastic outer skin/container, but it is noted that it may be used without such outer skin/container if the structural integrity of the shielding substance is adequate and non-harmful in contact with the patient.

Such shielding filler materials may include but are not limited to: liquids such as water and other fluids, viscous gels such as those made with carbomer, carbopol, xanthan gum and gelatin, or gelatinous materials such as silicones and alginates, or flexible or semi-rigid, or moldable firmer compounds such as alginates, silicones, putties, epoxy materials, or supersaturated crystal-forming liquids.

In most preferred embodiments, the shielding material may be encapsulated in an enclosing skin, (hereinafter referred to as a "bag" or "container" so as not to confuse this term with the skin or flesh of the patient) of flexible, tear-resistant material suitable for contact with the patient. The bag or container also should be able to tolerate high-level disinfection or sterilization and short-duration radiation exposure as would be experienced during a procedure.

The low-density contents of the bag/container may include materials that exhibit inherent viscosity that could be supplied in their final form in the bag. Other suitable content materials are available in powdered form and take on their useful viscous or deformable properties after mixing with a secondary fluid or fluids introduced prior to use.

Mixing these materials for the bag may be done separately, externally to the bag, and then introduced into the bag for use. Alternatively, some add-in viscosity enhancing component(s) may be shipped to the site of use within the bag, whereupon the (se) additional activating substance(s) could be added into the bag, sealed in place, then agitated sufficiently, thus mixing the subcomponents to create the finished conformal shielding material.

For some compounds put into the bag, additional heating may be required to allow such catalysis to proceed. A class of materials may be catalyzed by the introduction of a mechanical or other secondary energy trigger to crystallize a fluid, such as a supersaturated fluid of sodium acetate, into a semi-rigid material. An example of such a material is found in reusable hand warmers.

These materials can be sealed in the bag at the time of manufacture and some can be re-liquified for successive uses by heating after use. It should be noted that a more flexible material has benefits during surgery in that a surgical instrument can locally deform the bag and its contents for unimpeded access. Herein, the bag may contain low density contents to provide radiation shielding properties.

While the system and method described are generally intended for human patients, the system and method are well suited for veterinary use (i.e. using on animals that include, but are not limited to companion animals, like dogs, cats, etc.).

Referring now to FIG. 1A, this figure illustrates an exemplary embodiment of a shield bag system 101 that has two lobes 50, 103 that are coupled together. According to a first exemplary aspect, the geometry of the first lobe 103 may include modified toroidal or doughnut-shaped form, or in medicine, similar to a pessary, having an adequate volume of material surrounding the exposed eye 106A to provide useful shielding effects. The first lobe 103 may further include an aperture 105 in the geometric center so shaped as to allow surgical access to and visibility of the eye 106 or treatment area.

It is desirable for the thickness of the first lobe 103 surrounding the aperture 105 to be greater than 10 mm in the area lateral to the radiation source's contact plane with the patient where possible. This aperture 105 may be round, oval or asymmetric in shape so as to conform to the shape of the exposed surface of the human eye 106A during brachytherapy, where the eyelids 107 are typically opened wider than normal with use of an ophthalmic speculum.

However, other applications beyond medical procedures for the eye 106 are possible and are included within the scope of this disclosure. Additional medical procedures could involve any portion of the human anatomy. Further, applications beyond the treatment of humans are possible, such as using the radiation shield in procedures involving animals (i.e. veterinary uses etc.).

In medical procedures for the human eye 106, the toroidally-shaped lobe (shield) 103 may be placed in position surrounding the eye 106A of the patient 10, who is typically in a supine position with a neck support in place to tilt the head lordotically, or slightly chin up, as to maximize visual and surgical access to the treatment site.

This results in placement of the toroidal lobe (shield) 103 on a sloping tissue surface inclined towards the lateral side of the patient's check and forehead. Thus, in most embodiments, where the lobe 103 has a liquid or gelatinous consistency, gravitational force will cause the shield to slip temporally, down the slope of the face, and thus out of position. To counteract this misplacement, features described in the following paragraphs and drawings were devised to assist in anchoring the SSSE so as to maintain its desired position, and without interfering with any surgical procedure(s) to be performed.

Referring again to FIG. 1A, the system 101 has two lobes 50, 103 connected together, where the first lobe 103 has the aforementioned modified toroidal/doughnut shape to surround the eye 106 of a human 10. Meanwhile, the other lobe 50 may be sized to be of sufficient mass to resist being pulled across the bridge 110 of the nose 112.

Each lobe 50, 103 may form an air-tight or liquid-tight seal for the filler material 800 (see FIG. 8) positioned within each lobe/container 50, 103. The air-tight or liquid-tight seals may become important when the shielding filler material 800 is in the form of a liquid and/or gel.

FIG. 1A further illustrates a fastener 15 for the system 101. Fasteners 15 may include, but are not limited to, a piece of surgical tape, double-sided/double-stick tape, glue, and other like adhesives. Fasteners 15 may be used in practice to affix the narrower midsection along the nose bridge 110 to secure the bag system 101 in place. While not visible in FIG. 1A (but see FIG. 1B) a narrow or thin cylindrical-like/shaped connection 109 may be present between the two lobes 50 & 103, such that the fastener 15 will hold the entire system 101 against the bridge 110 of the nose 112.

An optional filler aperture 25 is shown at the left of the system 101 for adding/filling-in the shielding material when the shielding material is in a gel and/or liquid form. The optional filler aperture 25 may be provided with a valve (not shown) when the shielding material is added/provided after manufacture of the system 101. In the alternative to a valve, a plug, constricting tie or clip, or other closing means may be employed to close the filling aperture 25 after the container 101 is filled with the shielding filler material 800 (see FIG. 8).

The first lobe 103 may have a variable width (W) or cross-section around its generally toroidal circumference, as shown in FIG. 1. For example, the first lobe 103 may have first width W1 dimension proximate to the bridge 110 of the nose 112 and proximate to a corner of the eye 106. This first width W1 may be significantly greater than or larger than a second width W2 of the first lobe 103.

The second width W2 of the first lobe 103 may be proximate to the lower region of the eye 106 as shown in FIG. 2. Typically, in a human 10, there is more elevated/higher tissue near W1 compared to the location of W2 as illustrated in FIG. 1. The widths W1, W2 may be adjusted for tissue height and may be dependent/unique to the geometry of a particular human 10 receiving the shield bag system 101.

The second lobe 50 of the shield bag system 101 may comprise a closed volume having an ellipsoid or egg-shaped three-dimensional geometry. Since the second lobe is designed to protect the second eye (not visible in FIG. 1), it may be also characterized as having an eye-shaped volume/container.

As noted previously, one end 20 of the second lobe 50 may comprise a filler aperture 25 that may include a valve (not shown). The filler aperture 25 via a valve may be opened to receive liquids, gels, or putty-like materials described previously, and then the valve may be closed once the second lobe 50 is filled with the shielding filler(s).

Figure 1B:
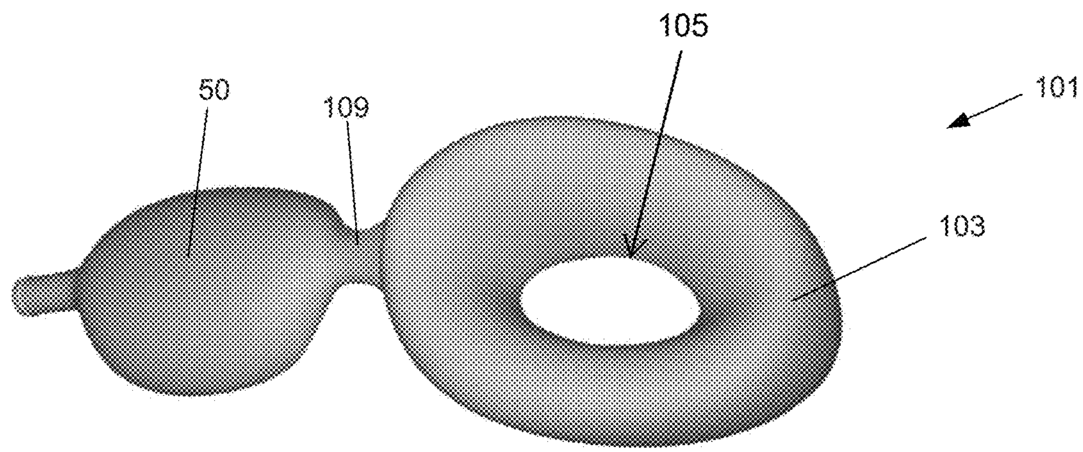
FIG. 1B illustrates an exemplary embodiment of the shield bag system of FIG. 1A that has two lobes but without a fastener provided over a cylindrical connection section present between the two lobes.

Referring now to FIG. 1B, this figure illustrates an exemplary embodiment of the shield bag system 101 that has two lobes 50, 103 but shown without a fastener 15 provided over a cylindrical connection 109 section present between the two lobes 50, 103. As illustrated in FIG. 1B, the first lobe 103 which is designed to cover the eye 106A (see FIG. 2A) receiving the medical treatment/procedure generally has a larger circumference and/or volume relative to the second lobe 50.

The second lobe 50 of the system 101 is designed to cover and protect a second eye 106B (see FIG. 2A) that is not receiving the medical treatment/procedure. The second lobe 50 may be designed to provide sufficient mass/weight to help anchor the shield bag system 101 across the bridge 110 of the nose 112.

Figure 2B:
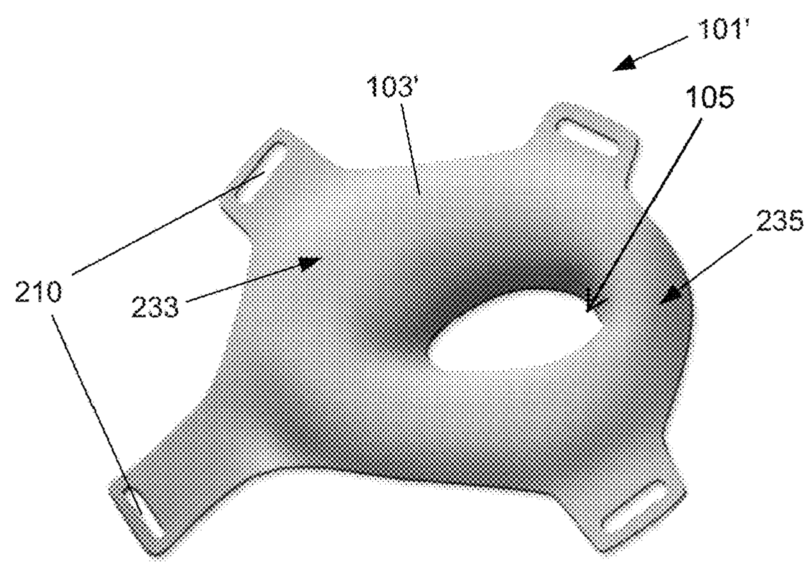
FIG. 2B illustrates an exemplary embodiment of the shield bag system of FIG. 2A that has one lobe but without fasteners and without the human being shown.
Figure 2A:
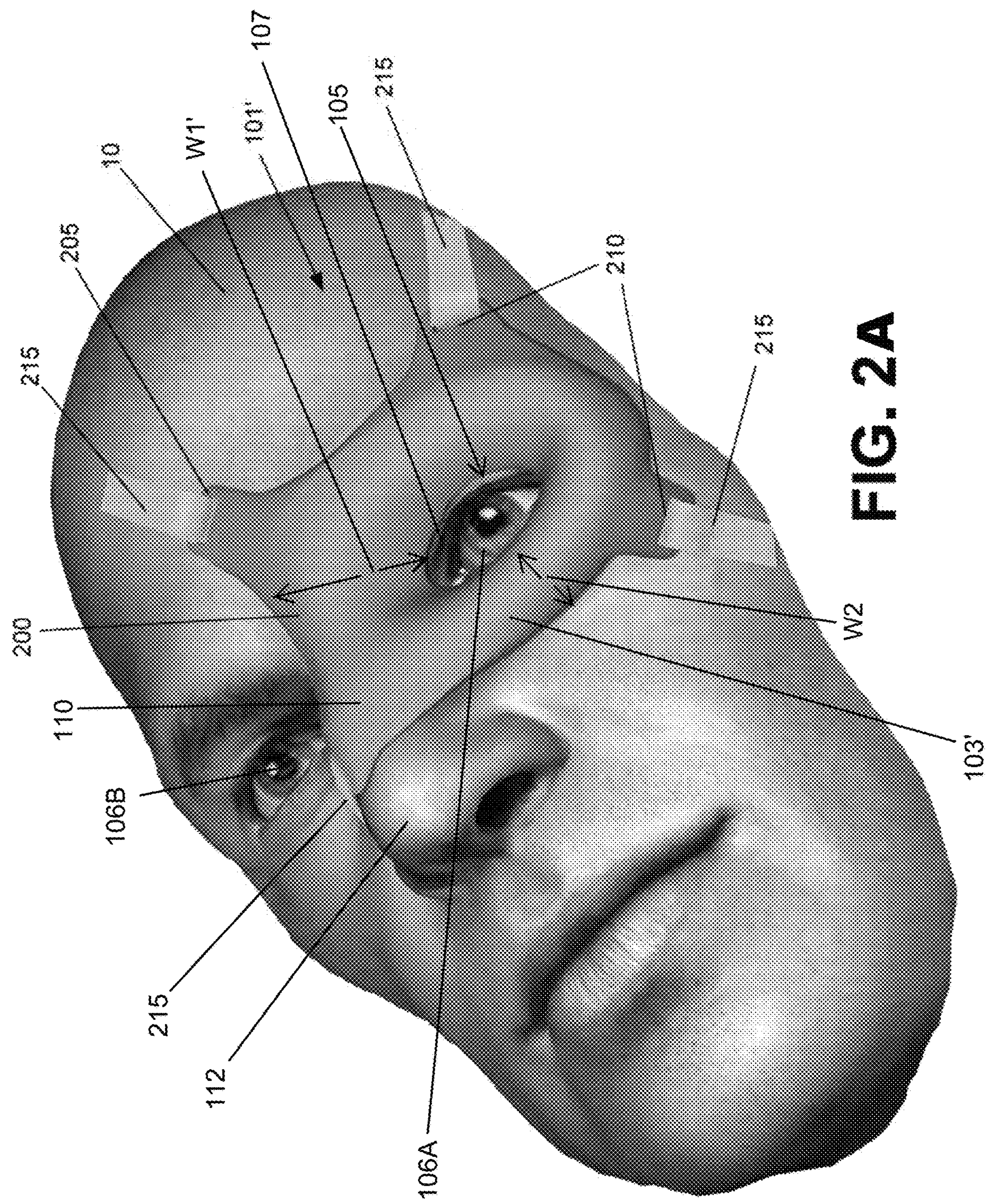
FIG. 2A illustrates a second exemplary embodiment of the shield bag system which has a series of peripheral tabs.

Referring now to FIG. 2A, this figure illustrates a second exemplary embodiment of the shield bag system 101' which has a series of peripheral tabs 205. According to this exemplary embodiment of FIG. 2A, the system 101' is a single lobe system meaning there is no second lobe 50 (such as illustrated in FIG. 1) and only includes the single lobe 103'. And because the system 101' does not have a second lobe 50, the second eye 106B is now visible compared to the exemplary embodiment of FIG. 1.

The system 101' of FIG. 2A may have at least four tabs 205, where each tab 205 may have a slot or hole 210 or other feature on it to allow the attachment of surgical tape 215. Other fasteners 215 besides surgical tape 215 are possible, and include, but are not limited to, a tie (not shown), or a clip (not shown) to allow anchorage of the shield bag system 101 in place on the human 10. The preferred exemplary embodiments are illustrated and use tape 215 as the fastener 215.

In an alternate exemplary embodiment (not shown), the slots or holes 210 within the tabs 205 may be eliminated, such that the anchoring tape 215 is simply adhered to the surface of the bag tabs 205. When slots or holes 210 are provided, these slots or holes 210 may have an elliptical shape or a rectangular shape where corners of the rectangle are rounded. Other geometries for the slots or holes 210 as well the tabs 205 are possible and are included within the scope of this disclosure.

According to this second exemplary embodiment of FIG. 2A, the system 101' may also have at least two different width dimensions W1', W2 similar to the embodiment of FIG. 1. As noted previously, single lobe 103' may have a variable width (W) or cross-section around its circumference, as shown in FIGS. 2A-2B.

For example, the single lobe/system 101' of FIG. 2A may have first width W1' dimension proximate to the bridge 110 of the nose 112 and proximate to a corner of the eye 106A. This first width W1' may be significantly greater than or larger than a second width W2 of the single lobe 103'. The second width W2 of the single lobe 103' may be proximate to the lower region of the eye 106A as shown in FIG. 2A.

Referring now to FIG. 2B, illustrates an exemplary embodiment of the shield bag system 101' of FIG. 2A that has one lobe 103' but without fasteners 205 and without the human patient 10 being shown. As illustrated in both FIGS. 2A-2B, the bag system 101' may have a thicker section/width 233 (W1') proximate to a corner of the eye 106A (see FIG. 2A) that is closest to the nose 112. Meanwhile, the bag system 101" may have a thinner section/width 235 (W2) furthest away from the nose 112 and opposite (or almost opposite) to the thicker section/width 233 (W1').

The thinner section 235 of FIG. 2B is generally positioned near the outside of a face geometry opposite the nose 112 or beneath the eye 106A, while the thicker section 223 is generally positioned closer and/or adjacent to the nose 112. It is noted that the exemplary embodiments of FIGS. 2A-2B are designed to treat the right eye 106A of a patient 10 (when facing the patient 10, and from the perspective of the medical practitioner facing the patient 10). When/if treating the left eye 106B of a patient 10, the geometry of the system 101' illustrated in FIGS. 2A-2B would be the mirror opposite as understood by one of ordinary skill in the art. This mirror opposite geometry needed for the right and left eyes 106A, 106B is applicable to all Figures described in this disclosure.

It is further noted that the geometry of the bag system 101' of FIG. 2B may not be identical to the geometry of the bag system 101' of FIG. 2A. The slight differences in geometry between the FIGS. 2A-2B demonstrate how the bag system 101 (throughout all Figures/Illustrations), in general, may be tailored/customized for each unique face geometry of a patient 10 as appropriate.

Figure 3A:
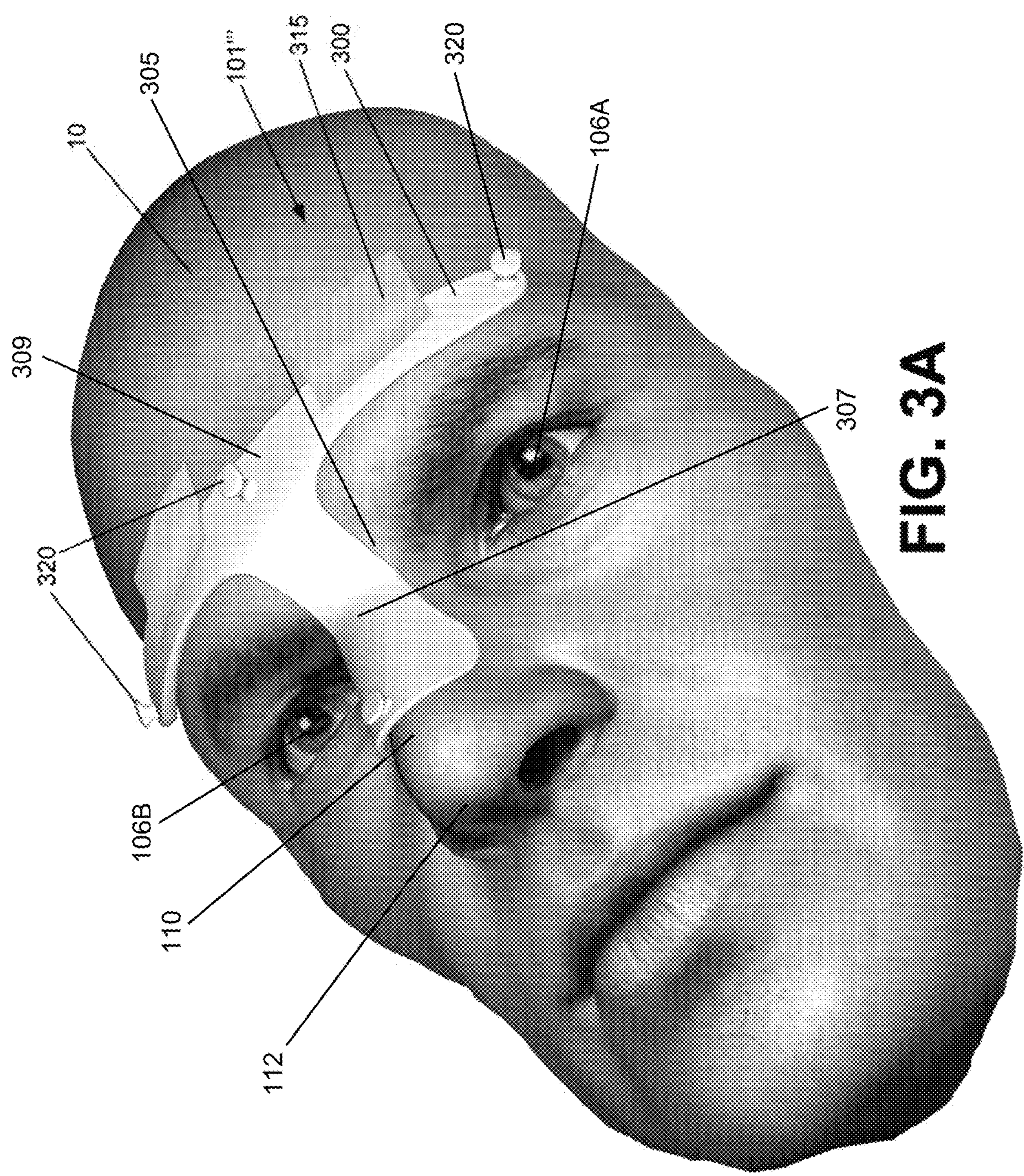
FIG. 3A illustrates a third exemplary embodiment for the bag system which may include a sterilizable mounting support that is anatomically shaped.

Referring now to FIG. 3A, this figure illustrates a third exemplary embodiment for the bag system 101" which may include a sterilizable mounting support 300 that is anatomically shaped. The support 300 may be anatomically shaped to lie along the bridge 110 of the nose 112 and across the brow ridge 305 of the human 10. Protruding from locations on this support are a series of hooks or pegs 320.

The support 300 may be characterized as having a "T-shaped" geometry. The vertical section of the T-shape may be formed by the first section/portion 307 positioned on the bridge 110 of the nose 112. Meanwhile, the horizontal section of the T-shape geometry may be formed by the section/portion 309 of the system 101" that is provided just above and across/in parallel with the brow ridge 305 of the human 10.

This support 300 may be affixed to the face of the human 210 using surgical tape 315. However, other fasteners 315, as described previously, may be employed and as desired. The shielding bag system 101" of FIG. 3B may include a series of tabs 305 having holes 310 in them to reliably engage with the aforementioned pegs or hooks 320 thus positively locating the bag system 101". Other fasteners/mechanisms 320 besides hooks, pegs, tabs, holes, etc. are possible and are included within the scope of this disclosure as understood by one of ordinary skill in the art.

That is, it would also be possible as part of this exemplary embodiment shown in FIG. 3A to create other shapes of mounting supports 320 that would additionally extend laterally across the check from an area near the tip of the nose 112, or in a configuration where a conformal, continuous frame surrounds the eye to provide additional anchor points below and lateral to the eye 106A, thus surrounding the SSSE bag system 101 on all sides for more extensive anchoring.

Figure 3B:
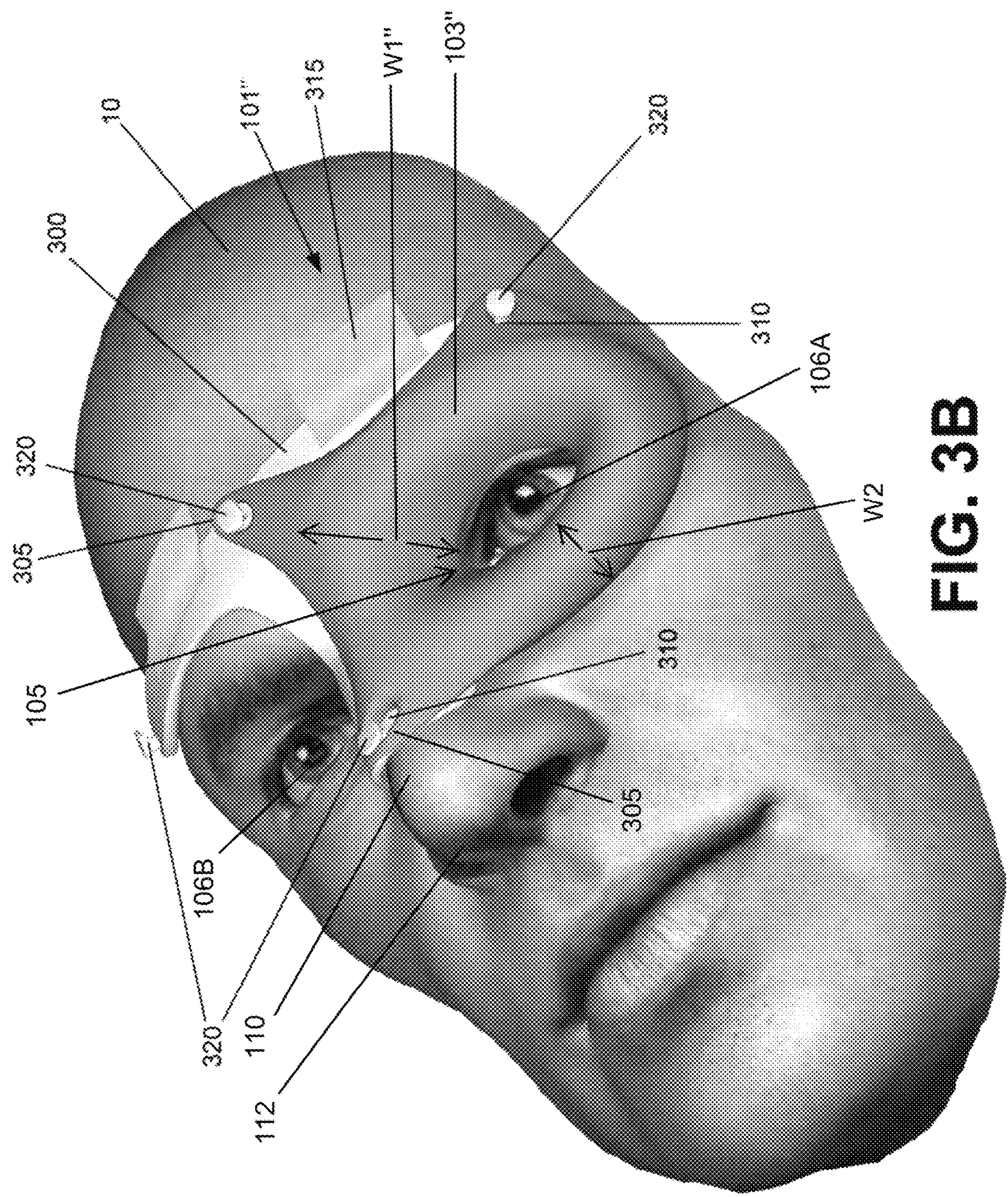
FIG. 3B illustrates the third exemplary embodiment for the bag system, where single lobe is present and coupled to the mounting support illustrated in FIG. 3A.

Referring now to FIG. 3B, this figure illustrates the third exemplary embodiment for the bag system 101", where the single lobe 103" is present and coupled to the mounting support illustrated in FIG. 3A. The single lobe 103" includes openings 310 which receive the mounting supports/fasteners/mechanisms 320.

Similar to the first and second exemplary embodiments of FIGS. 1-2, the single lobe 103" of FIG. 3B may also have at least two different width dimensions W1", W2 around its circumference to match the geometry of the eye socket for the eye 106A. As noted previously, lobe 103" may have a variable width (W) or cross-section around its generally toroidal shaped circumference, as shown in FIG. 3B.

Figure 4C:
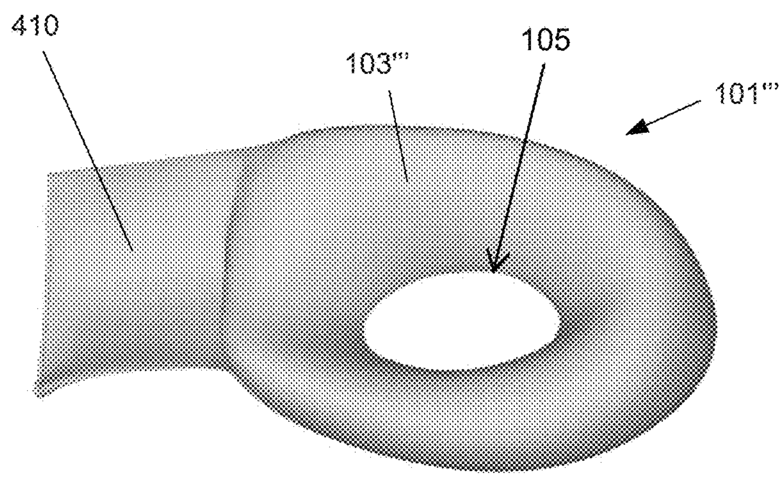
FIG. 4C illustrates an exemplary embodiment of the shield bag system of FIG. 4B that has one lobe but without any fasteners, the clamp, mounting support, or human patient.
Figure 4A:
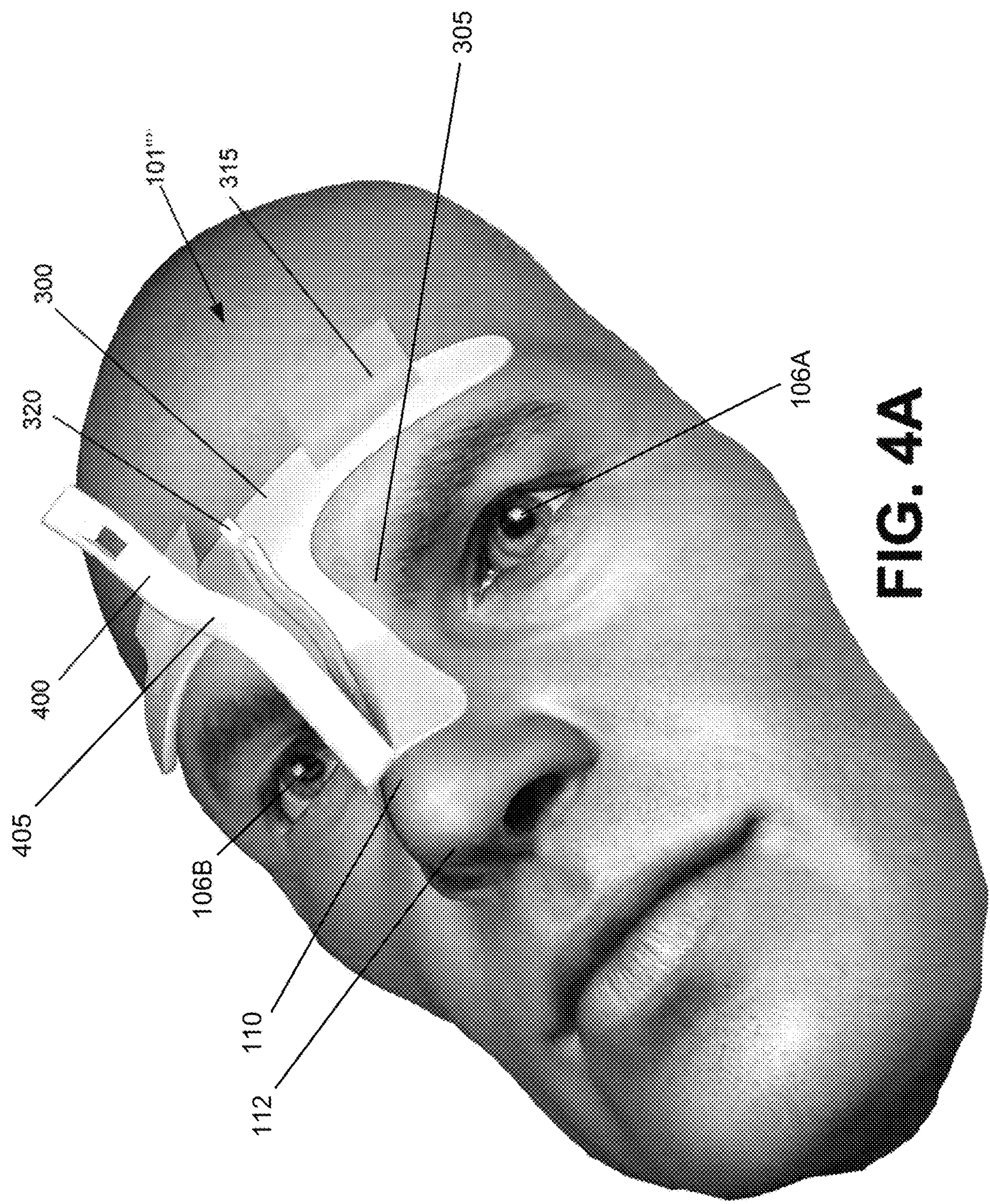
FIG. 4A illustrates a fourth exemplary embodiment of the bag system which may include a similar mounting support illustrated in FIGS. 3A-3B, but with the addition of a hinged clamping bar.

Referring now to FIG. 4A, this figure illustrates a fourth exemplary embodiment of the bag system 101"" which may include a similar mounting support 300 illustrated in FIGS. 3A-3B, but with the addition of a hinged clamping bar 400. This clamping bar 400 may be brought down and latched, capturing a thinned extension 410 (see FIG. 4B) of the shielding material's bag system 101'" above the bridge of the nose. The main portion or lobe 103"" of the bag system 101'" may be provided on the other side of the bridge of the nose, opposite the thinned extension 410.

Figure 4B:
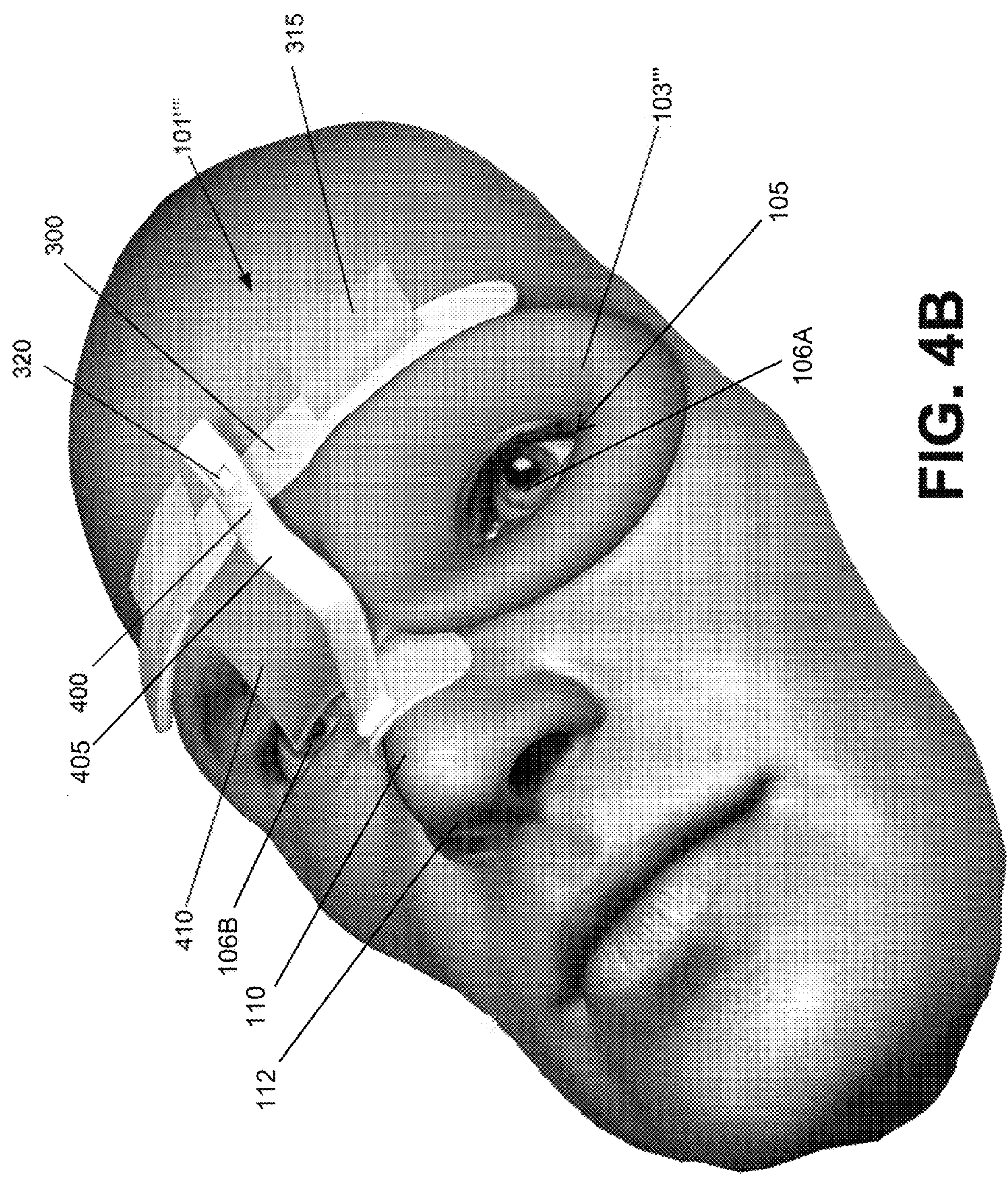
FIG. 4B illustrates the clamping bar of FIG. 4A brought down and latched relative to FIG. 4A.

Referring now to FIG. 4B, this figure illustrates the clamping bar 400 of FIG. 4A brought down and latched relative to FIG. 4A. In practice, this clamping bar 400 could form the seal to contain the shielding material contents within the bag system 101'", or instead, a secondary sealing clip, (not shown) could be used to form a closure along the portion of the bag system 101'" extending away from the bridge 110 of the nose 112 on the side opposite the toroidal shielding portion.

The clamping bar 400 may include a curved section 405 that mirrors/has an angle similar to the angle the bridge 110 of the nose 112 may have relative to the brow ridge 305. That is, the curved section 405 may mirror the geometry formed between the bridge 110 of the nose 112 and the brow ridge 305, which is known to one of ordinary skill in the art.

Additionally, peg and hole/tab features 320, as described in the third embodiment above, could be added to the design to add additional support across the brow ridge 305 (see FIG. 4A) above the eye 106A, and additionally across the cheek below the eye 106A if needed.

Referring now to FIG. 4C, illustrates an exemplary embodiment of the shield bag system 101'" of FIG. 4B. The bag system 101'" illustrated in FIG. 4C has one lobe 103'" and is shown without any fasteners 315, the clamp 400, mounting support 300, or human patient 10 in this figure.

As noted previously, this system 101''' of FIG. 4 may have a thinned extension 410 that is designed to cover and/or protect the left eye 106B which is not receiving the medical treatment/procedure. The extension 410 may be enlarged or decreased compared to the relative dimensions illustrated in FIGS. 4A-4C without departing from the scope of this disclosure as understood by one of ordinary skill in the art. Similarly, the relative dimensions of all Figures in this disclosure may be enlarged or decreased without departing from the scope of this disclosure.

Figure 5:
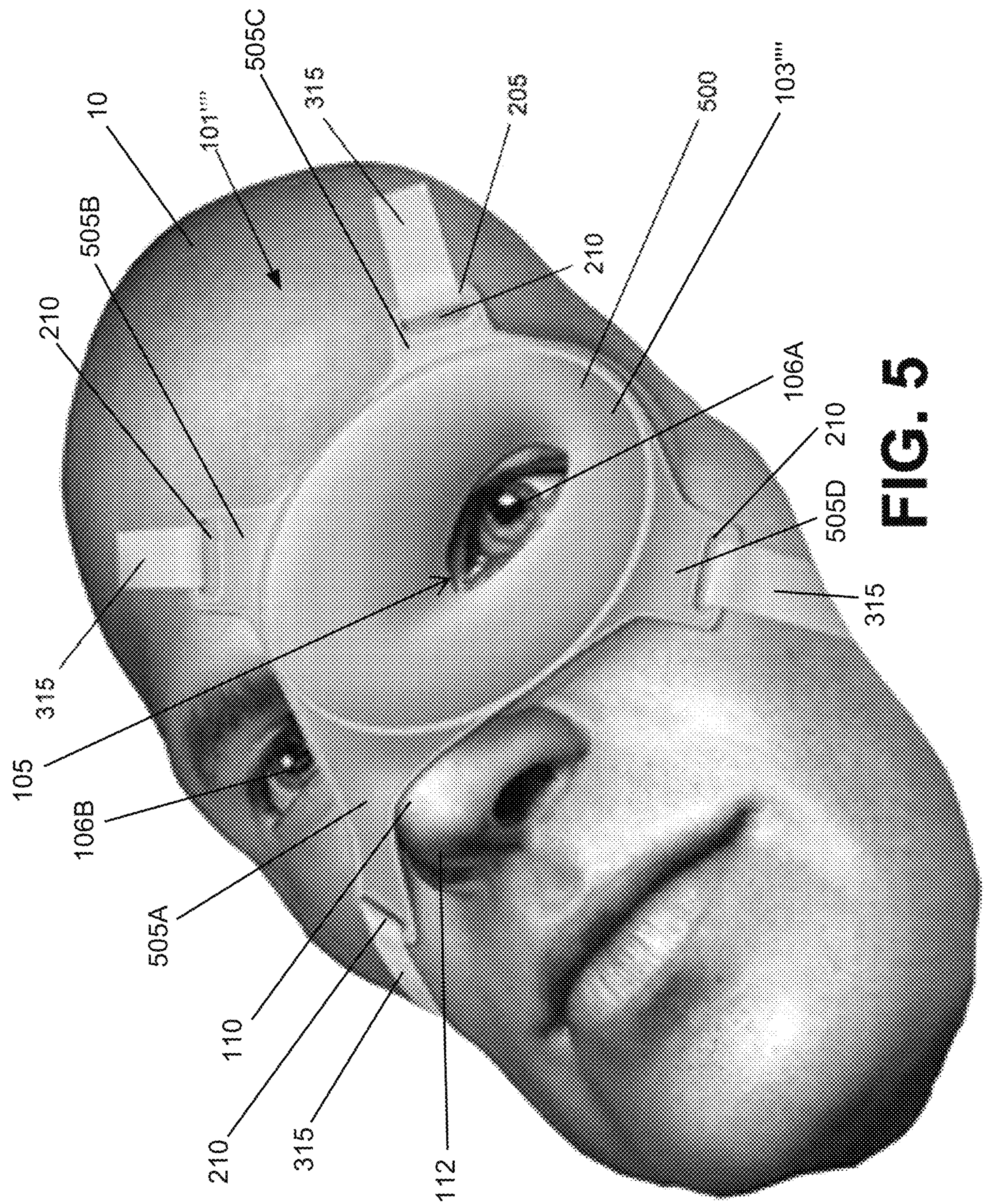
FIG. 5, illustrates a fifth exemplary embodiment that may comprise a heat-sealed shielding bag system.

Referring now to FIG. 5, this figure illustrates a fifth exemplary embodiment that may comprise a heat-sealed shielding bag system 101''''. The material that is heat-sealed together to form this bag may be blown or sucked into a mold prior to sealing such that the contours and protruding volume would be adequate to create the proper volume and initial shape of the bag system 101''''. The bag system 101'''' may have a single lobe 103''''' with a toroidal shaped main body that encloses or contains a pliable putty or epoxy type materials.

The bag system 101'''' may include substantially flat tabs 505 with slots 210 that extend from the single lobe 103'''' where fasteners 215 may be placed through the slots, similar to other exemplary embodiments. Specifically, the bag system 101'''' may have about four flat tabs 505 of variable lengths that extend over the face of the patient 10. A first flat tab 505A can have a first length, while three other flat tabs 505B, 505C, 505D may have second lengths shorter/smaller than the first length.

Figure 6:
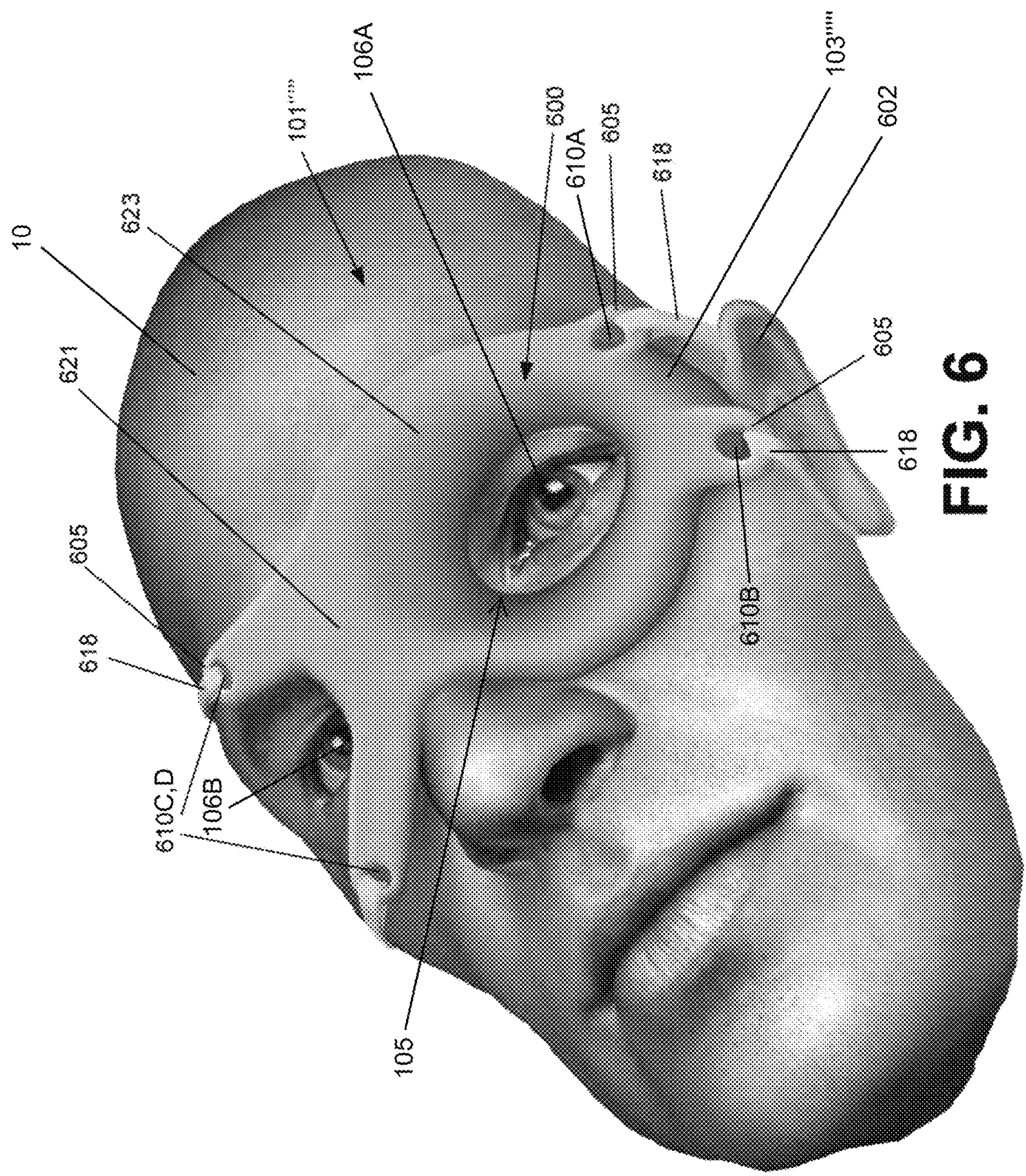
FIG. 6 illustrates a sixth exemplary embodiment of the bag system which may include a heat-sealed bag having multiple laterally placed tabs that allow for coupling to an ear of the patient.

Referring now to FIG. 6, this figure illustrates a sixth exemplary embodiment of the bag system 101''''' which may include a heat-sealed bag 600 having multiple laterally placed tabs 605 that may allow for coupling to one or both cars 602 of the patient 10. Each tab 605 may have a slot or hole 610 near their extremity to allow strands of material such as a cord or webbing 618, or clips (not shown) to be attached to the patient 10. The system 101''''' may include a single lobe 103''''' similar to other lobes 103 described previously.

These fasteners 618 may anchor the shielding bag 600 in place by providing a loop around the car such as is used on face masks. Also illustrated in FIG. 6 is a configuration where the portions 621, 623 of the shield bag superior and inferior to the eye are extended to provide greater coverage; this extended configuration may be utilized only superiorly or inferiorly as well. As illustrated in FIG. 6, the first set of tabs 605 having a first set of slots 610A, 610B may be coupled directly with the lobe 103'''''.

Meanwhile, a second set of tabs 605 with a second set of slots 610C, 610D may be positioned furthest away from the lobe 103''''', opposite to the first set of slots 610A, 610B. The second set of tabs 605 with the second set of slots 610C, 610D may extend across the second eye 106B which is not receiving the medical procedure. The second set of tabs 605 with slots 610C, 610D may extend at angles, such that the second eye 106B is not blocked by these structures.

Manufacturing and Materials

The Bag

The bag system 101 can be made of any tear-resistant, flexible or pliable, and sterilizable material. The material properties should be such that when the bag system 101 containing the shielding filler material is placed upon the patient 10, it will generally conform to the uniquely shaped contours/geometry of that patient 10. This is to prevent gaps between the skin and the shielding bag system 101 that would allow radiation to escape the treatment site in a generally lateral direction (relating to the general plane of contact between the radiation source and the patient's tissues.)

The bag system 101 may be made from elastic materials that are found in surgical gloves, such as latex silicone and nitrile, or they can be made from autoclavable pliable film materials such as polypropylene. It is understood that other polymer films having flexibility and sterilizability may also be utilized as materials for the bag system 101. For the elastic materials, the methods of production may include pouring into a two-part mold, the excess being poured out, then left to cure, followed by removal from the mold.

Other molding techniques such as rotational molding may be used as well to fuse powdered polymeric materials into the pliable, contoured shapes needed. For the pliable plastic film materials, thermoforming by open molding with pressure or suction assist followed by heat sealing is a useful approach. Blow molding may also be used to produce a more seamless finished product.

The Bag System Contents

The low-density contents 800 (see FIG. 8) of the bag system 101 will usually be common liquids such as water, or pliable or moldable materials so as to conform to the unique contours of the patient 10 in use. As noted above, the low-density contents 800 of the bag system 101 may include materials that exhibit inherent viscosity that could be supplied in their final form in the bag system 101. Other suitable content materials 800 are available in powdered form and take on their useful viscous or deformable properties after mixing with a secondary fluid or fluids prior to use.

Mixing these shielding filler materials 800 for the bag system 101 may either be done separately, externally to the bag, and then introduced into the bag system 101 for use. Alternatively, some components/shielding filler materials 800 may be shipped to the site of use for the bag system 101 whereupon additional activating substance(s) 800 could be added into the bag system 101, sealed in place, then agitated sufficiently thus mixing the subcomponents to create the finished conformal shielding material 800.

For some compounds 800 put into the bag system 101, additional heating may be required to allow a catalysis to proceed. A class of materials may be catalyzed by the introduction of an energy trigger to crystallize a fluid, such as a supersaturated fluid of sodium acetate, into a semi-rigid material. An example of such a catalyzed material is found in reusable hand warmers.

These shielding filler materials 800 can be sealed in the bag system 101 at the time of manufacture, and some can be re-liquified for successive uses by heating after use. It should be noted that a more flexible material 800 has benefits during surgery in that a surgical instrument can locally deform the bag system 101 and its contents for unimpeded access. Herein, the bag system 101 may contain low-density contents 800 to provide radiation shielding properties.

These contents 800 may have the capacity to maintain a novel shape when molded by the operating surgeon or health care personnel. The capability may be intrinsic to the physically malleable low-density material, or the low-density contents may be manipulated so as to conform to a rigid mold while it sets into the desired shape.

Attachment to the Targeted Area

The bag system 101 system usually must be attached so as to surround the targeted area and remain in place during use. Methods of attachment may include, but are not limited to, a harness, tape, straps (e.g., string, plastic, webbing), glue, and other like adhesives. These methods are devised so as not to harm the fellow/neighboring eye 106B by weight, or physically traumatize the fellow/neighboring/non-treated eye 106B. Much like a mask, strings, straps or elastic 618 (see FIG. 6) may connect and center the bag system 101 around the eye 106A so as to maintain its position surrounding the brachytherapy target (i.e. eye 106A). The attachments/fasteners 315, 618 usually must be made from low-density materials as to avoid the production of unnecessary bremsstrahlung radiation, as described previously.

Figures 7A, 7B, 7C, 7D:
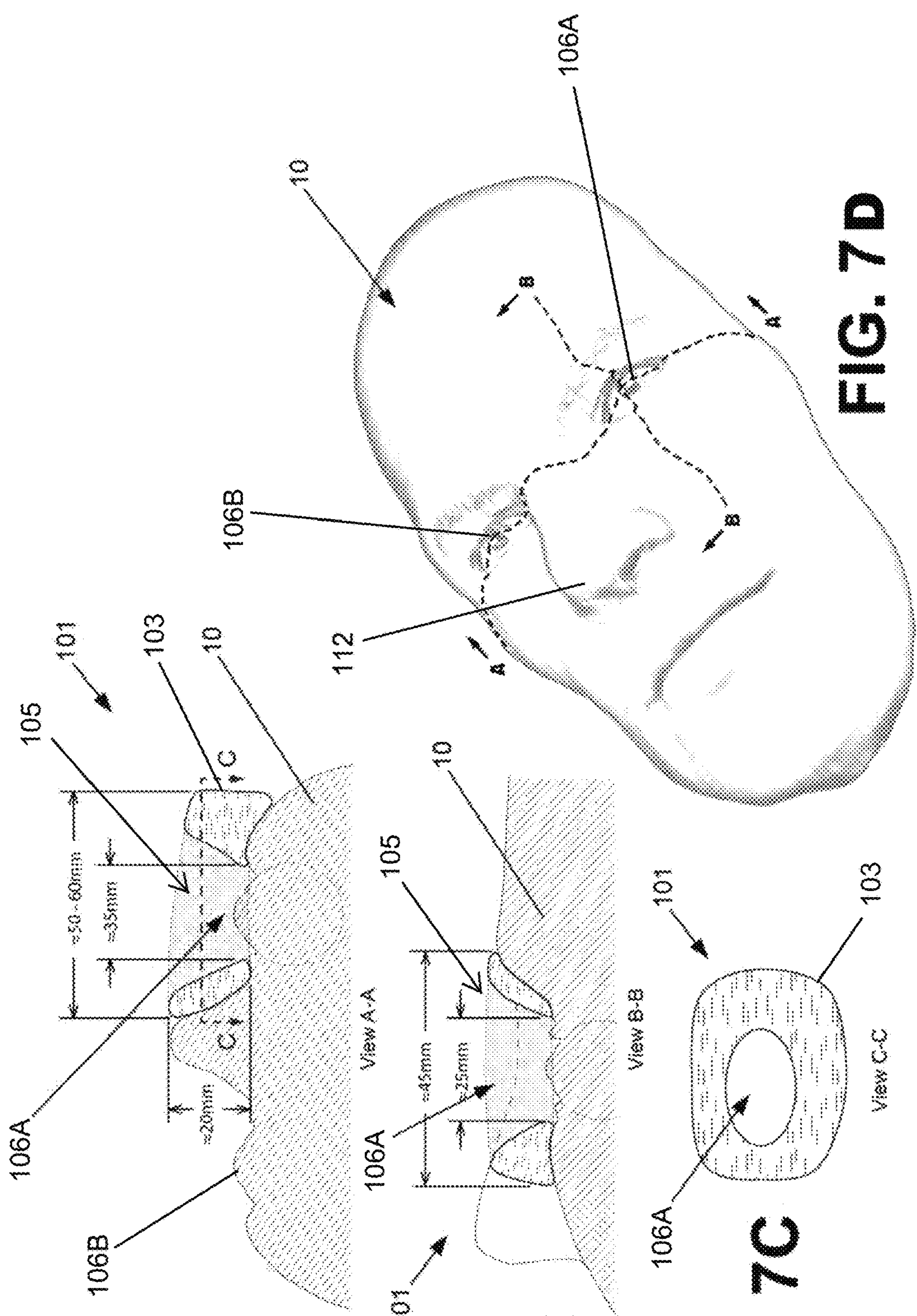
FIG. 7A illustrates the cross-sectional view of the human patient taken along the sectional line A-A of FIG. 7D.
FIG. 7B illustrates the cross-sectional view of the human patient taken along the sectional line B-B of FIG. 7D.
FIG. 7C illustrates the cross-sectional view of the bag system taken along the sectional line C-C of FIG. 7A.
FIG. 7D illustrates a side perspective view of a human patient and cross-sectional view lines which are referenced and illustrated in FIGS. 7A-7B.

Referring now to FIG. 7D, this figure illustrates a side perspective view of a human patient 10 and cross-sectional view lines which are referenced and illustrated in FIGS. 7A-7B. FIG. 7A illustrates the cross-sectional view of the human patient 10 taken along the sectional line A-A of FIG. 7D. FIG. 7A further illustrates the main aperture 700 of the bag system 101 which may receive medical instruments that have a radioactive source for providing therapeutic radiation treatments/therapy.

Referring now to FIG. 7A, this figure illustrates the cross-sectional view of the human patient 10 taken along the sectional line A-A of FIG. 7D. FIG. 7A illustrates exemplary dimensions for the system 101. These dimensions are only examples. It is noted that the dimensions for the lobe 103 may vary from each cross-sectional view due to the asymmetrical shape/geometry of the lobe 103 as understood by one of ordinary skill in the art.

The lobe 103 of FIG. 7A for this cross-sectional view may have an internal diameter of about 35.00 mm, and an outer diameter between about 50.00 mm to about 60.00 mm. The thickness or height of the lobe 103 along this cross-sectional view may be about 20.00 mm. One of ordinary skill in the art recognizes that dimensions greater or smaller than those illustrated in the Figures are possible and are included within the scope of this disclosure. Also in FIG. 7A, a sectional line C-C is further illustrated and will be described below in connection with FIG. 7C.

Referring now to FIG. 7B, this figure illustrates the cross-sectional view of the human patient 10 taken along the sectional line B-B of FIG. 7D. FIG. 7B illustrates exemplary dimensions for the system 101 in this cross-sectional view. The lobe 103 according to this cross-sectional view may have an outer diameter of about 45.00 mm, and an inner diameter of about 25.00 mm. As noted previously, the dimensions for each lobe 103 may vary from each cross-sectional view due to the asymmetrical shape of the lobe 103 as understood by one of ordinary skill in the art.

Referring now to FIG. 7C, this figure illustrates the cross-sectional view of lobe 103 taken along the sectional line C-C of FIG. 7A. FIG. 7C is a cross-sectional view of a top/upper portion of the bag system 101 as illustrated in FIG. 7A. As noted above, the lobe 103 may be asymmetrical along most axes of geometry. But it is possible, and within the scope of this disclosure, to create a lobe 103 which does have symmetry along one or more axes of geometry for the structure.

Figure 8:
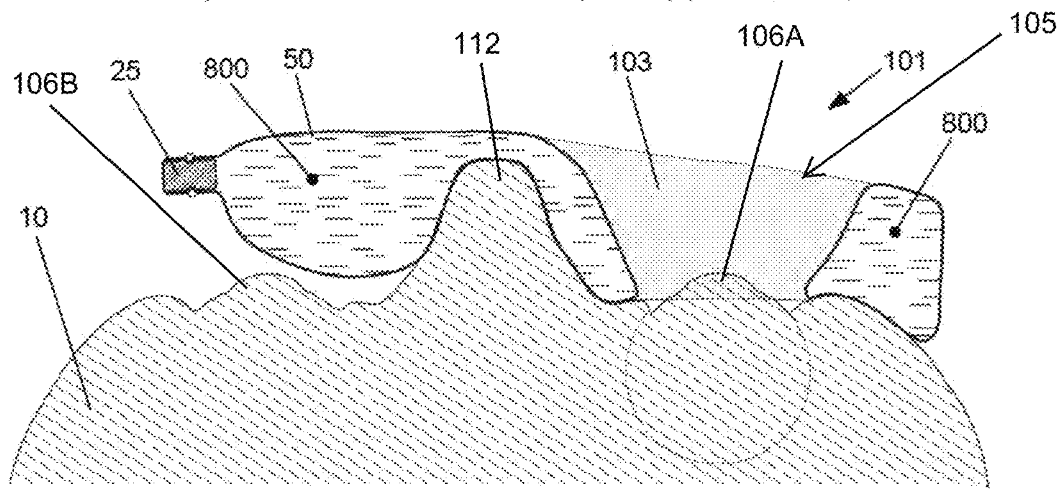
FIG. 8 illustrates a cross-sectional view of the bag system that is also illustrated in FIGS. 1A-1B.

Referring now to FIG. 8, this figure illustrates a cross-sectional view of the bag system 101 that is also illustrated in FIGS. 1A-1B described above. The first lobe 103 of the system 101 and having a toroidal/doughnut shape is visible. The second lobe 50 and which is positioned over the eye 106B not being treated is also visible. The filler aperture 25 is also shown in FIG. 8. Further, the shielding filler material 800 for the bag system 100 is also visible in this view.

As noted previously, the shielding filler material 800 may include but is not limited to: liquids such as water and other fluids, viscous gels such as those made with carbomer, carbopol, xanthan gum and gelatin, or gelatinous materials such as silicones and alginates, or flexible or semi-rigid, or moldable firmer compounds such as alginates, silicones, putties, epoxy materials, or supersaturated crystal-forming liquids.

Figure 9:
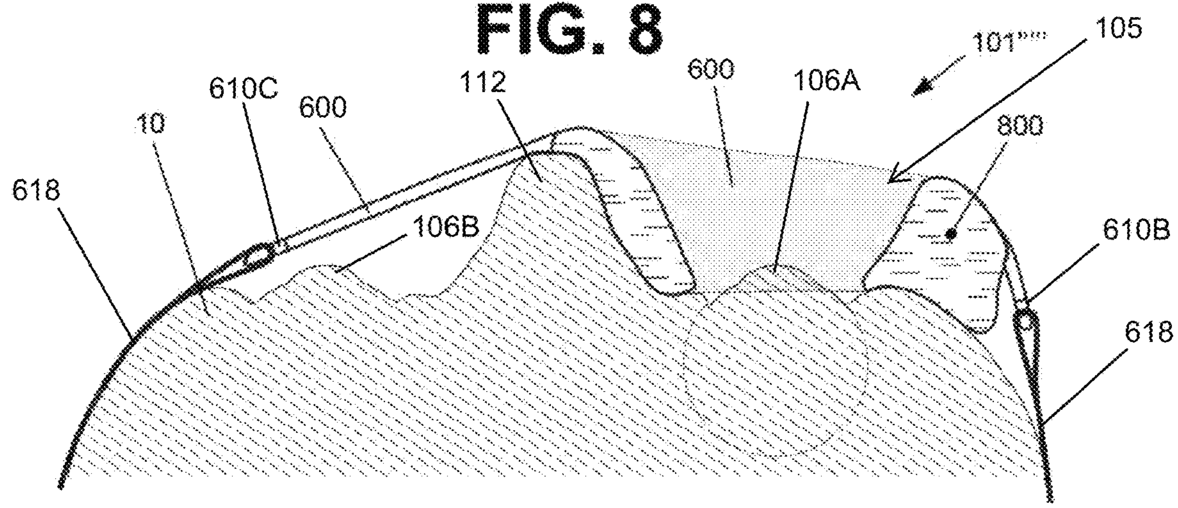
FIG. 9 illustrates a cross-sectional view of the bag system also shown in FIG. 6.

Referring now to FIG. 9, this figure illustrates a cross-sectional view of the bag system 101"''' also shown in FIG. 6. Also visible in FIG. 9 are the shielding filler material 800 as well as the cord or webbing 618 which fastens the system 101"''' to the cars 602 (not visible in FIG. 9, but see FIG. 6) of the patient 10.

Figure 10:
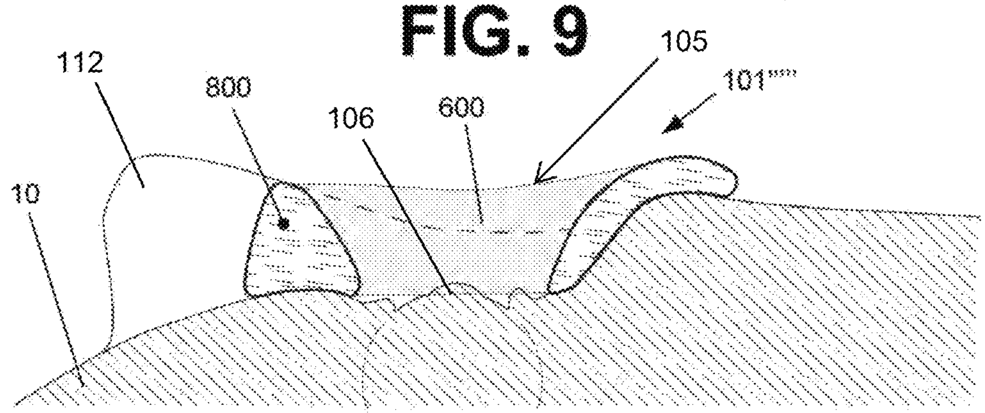
FIG. 10 illustrates another cross-sectional view of the bag system also shown in FIG. 6 and in FIG. 9 described above.

Referring now to FIG. 10, this figure illustrates another cross-sectional view of the bag system 101"''' also shown in FIG. 6 and in FIG. 9 described above. The shielding filler material 800 enclosed by the bag system 101"''' is also visible in this FIG. 10.

Figure 11:
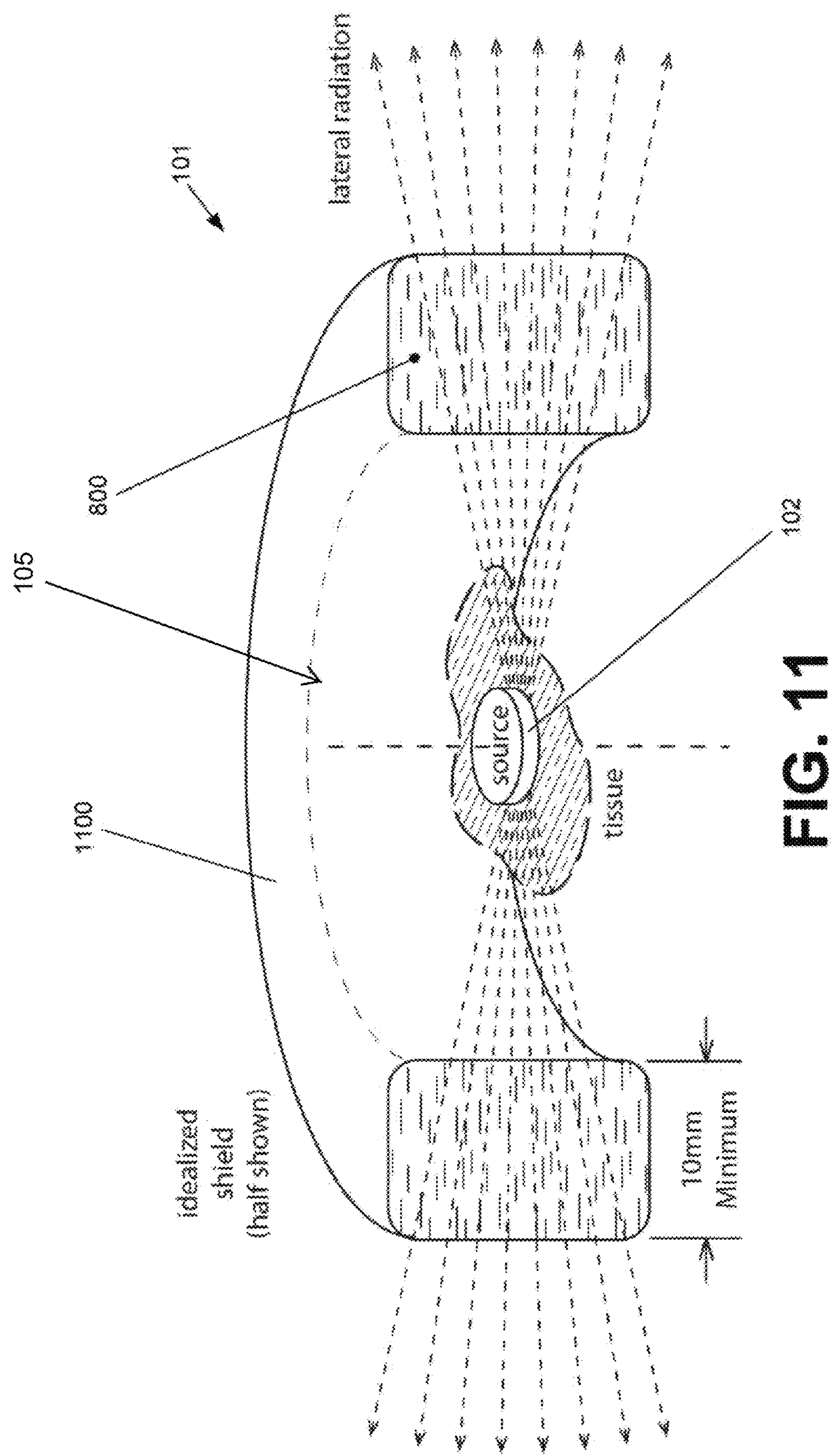
FIG. 11 illustrates a radiation source which emits beta or low-energy gamma radiation and which may be blocked by the exemplary shielding system.

Referring now to FIG. 11, this figure illustrates a radiation source 102 which emits beta or low-energy gamma radiation and which may be blocked by the exemplary shielding bag system 101, which is illustrated as a ring 1100 in this Figure.

The shielding filler material 800 is also visible in the view of FIG. 11. Only the laterally projected radiation from the radiation source 102 is schematically shown in FIG. 11 for clarity of concept. This radiation source 102 may be coupled to a medical instrument, such as the iWand® brand of medical instrument sold by the assignee as of this writing which is described in one or more commonly assigned U.S. Pat. Nos. 10,173,075; 10,117,578; and 11,020,000, the contents of which are hereby incorporated by reference.

Also shown are exemplary relative sizes of the source and ring 1100. FIG. 11 also provides exemplary dimensions for the system 101, such as an exemplary width of the shielding ring 1100. The exemplary width (W) notation (i.e. of about 10.0 mm width) for the ring 1100 in FIG. 11 is a target width (W). In production, the presence of the brow ridge 305 (see FIG. 3A) or bridge 110 of the nose 112 (see FIG. 3A) may not allow a full width of 10.0 mm to be met when the system 101 is built for specific sizes/specific human patients 10 which may have different sized brow ridges 305 and/or nose bridges 110.

As noted previously, all dimensions disclosed herein are only examples. One of ordinary skill in the art recognizes that dimensions greater or smaller than those illustrated in the Figures are possible and are included within the scope of this disclosure.

Figure 12:
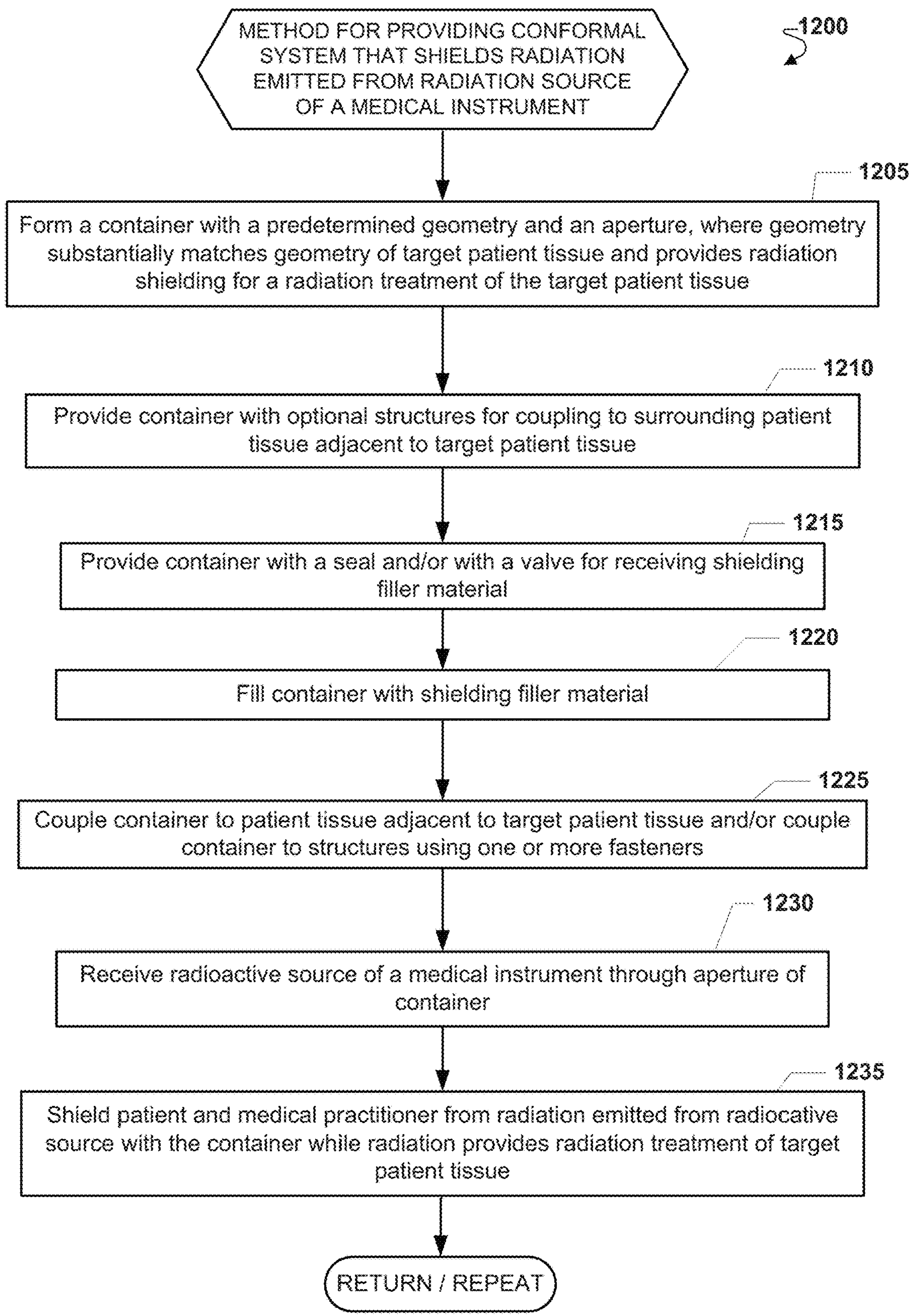
FIG. 12 illustrates an exemplary method for using the structures of FIGS. 1-11 to provide a conformal system that shields radiation emitted from a radiation source of a medical instrument.

Referring now to FIG. 12, this figure illustrates an exemplary method 1200 for using the structures of FIGS. 1-11 to provide a conformal system 101 that shields radiation emitted from a radiation source 102 of a medical instrument. Step 1205 is the first step of the exemplary method 1200 of FIG. 12.

In step 1205, a container or bag system 101, such as any of the ones illustrated in FIGS. 1-11, having a predetermined geometry and an aperture 105 is formed. The geometry of the container 101 generally matches the geometry/contours of target patient tissue 106A and provides radiation shielding for a radiation treatment of the target patient tissue 106A. The target patient tissue, according to this exemplary system 101, is a human eye 106A. However, other patient tissue 106 besides human eyes are possible and are included within the scope of this disclosure. Other patient tissue could include a human head, torso, arms, legs, feet, hands, etc.

The radiation source 102 is a type that emits beta-particles, while the container system 101 shields the radiation with low-density materials. As noted previously, in the case of beta radiation, such low-density materials do not abruptly reduce the particles' velocity, and generally do not create significant amounts of unwanted and potentially hazardous bremsstrahlung x-rays.

Next, in step 1210, the container 101 may be provided with optional structures (i.e. connection 109 of FIGS. 1A-1B; slots or holes 210 of FIGS. 2A-2B; support 300 of FIG. 3A; holes 310 of FIG. 3B; etc.) for coupling to surrounding patient tissue (i.e. nose 112, cheeks, brow ridge 305) that is adjacent to the target patient tissue 106A.

Subsequently, in step 1215, the container 101 may be sealed and/or provided with a valve or stem 25 that may receive shielding filler material 800 that may be in the state/form of a liquid, gel, or putty-like material. The seal of the container 101 may make the container 101 air-tight and/or fluid-tight.

Next, in step 1220, the container 101 may be filled with the shielding filler material 800. As noted previously, the shielding filler material 800 may include, but is not limited to, water, carbomer, carbopol, xanthan gum and gelatin, gelatinous materials including a silicone and an alginate, and flexible or semi-rigid, or moldable firmer compounds such as alginates, silicones, putties, epoxy materials, or super-saturated crystal-forming liquids.

After step 1220, in step 1225, the container 101 may be coupled to patient tissue (i.e. nose 112, cheeks, brow ridge 305) that is adjacent to the target patient tissue 106A using one or more fasteners (i.e. tape 15, 215, 315; support 300; clamping bar 400; cord or webbing 818). The fasteners could include an adhesive substance in addition to mechanical structures as understood by one of ordinary skill in the art In step 1230, the container 101 may receive the radioactive source 102 of a medical instrument through the aperture 105 of the container. Next, in step 1235, the patient 10 and medical practitioner (not illustrated) are shielded from radiation being emitted from the radioactive source 102 with the container 101 while radiation provides radiation treatment of target patient tissue 106A. Thus, the container 101 shields the patient 10 and the medical practitioner from beta-particles emitted from the radiation source with its low-density materials which do not abruptly reduce the beta-particles' velocity, and generally do not create significant amounts of unwanted and potentially hazardous bremsstrahlung x-rays.

Certain steps in the processes and/or methods described above, including method 1200, are enabled by this specification and naturally precede others for the invention to function as described. However, the invention is not limited to the order of the steps described if such order or sequence does not alter the functionality of the inventive system 101.

That is, it is recognized that some steps may be performed before, after, or parallel (substantially simultaneously with) other steps without departing from the scope and spirit of inventive system 101. In some instances, certain steps may be omitted or not performed without departing from the invention. Further, words such as "thereafter", "then", "next", etc. are not intended to limit the order of the steps. These words are simply used to guide the reader through the description of the exemplary method.

It is noted that several of the figures provide exhaustive detail which would allow one of ordinary skill in the art to make, build, and use the inventive system as intended. Thus, the several figures of this disclosure are enabling to one of ordinary skill in the art.

Alternative embodiments for the system and method of the present disclosure will become apparent to one of ordinary skill in the art to which the method and system pertain without departing from the scope of this disclosure. For example, several of the exemplary embodiments may be combined together and/or parts and/or sections of various embodiments may be interchanged without altering the scope of this disclosure. As but one example, the fasteners 618 comprising cord or webbing of FIG. 6 could be switched out with the fasteners 15, 215, 315 comprising adhesive tape of FIGS. 1A, 2A, 3A—and vice-versa.

Therefore, although selected aspects have been illustrated and described in detail, it will be understood that various substitutions and alterations may be made therein without departing from the scope of the present disclosure, as defined by the following claims.

What is claimed is:

1. A conformal system for radiation shielding of tissue surrounding a human eye, comprising:
- a container made of a first material that defines a volume, where the volume has a seal for containing a filler material;
- the filler material being provided within the volume defined by the container, the filler material comprising a second material different from the first material; both the first and second materials provide shielding against beta particle or low energy gamma radiation; and
- the container further defining an eye-shaped aperture with two corners such that an object may pass through the eye-shaped aperture, while the container maintains its seal for the filler material, the eye-shaped aperture having a first perimeter that is equal to or greater than a second perimeter of the human eye; and
- the container being configured to be positioned adjacent to and flexibly conform to an anatomy of an area of a human face surrounding the human eye.

2. The system of claim 1, wherein the container further comprises at least one tab and a hole for receiving a fastener.

3. The system of claim 1, wherein the first material comprises at least one of: a solid material that is a flexible and tear-resistant, and a material suitable for contact with skin.

4. The system of claim 1, wherein the second material comprises at least one of: a liquid, gel, or pliable material.

5. The system of claim 1, wherein the second material comprises at least one of: water, carbomer, carbopol, xanthan gum, gelatin, gelatinous materials, a silicone, an alginate, and flexible or semi-rigid, or moldable firmer compounds.

6. The system of claim 1, wherein the container comprises a generally toroidal geometry.

7. The system of claim 1, wherein the container is for a medical procedure involving the eye.

8. The system of claim 7, wherein the aperture of the container may receive a medical instrument which has a beta particle or low energy gamma radiation source.

9. The system of claim 1, wherein the container comprises a first lobe and a second lobe.

10. A conformal system for radiation shielding of tissue surrounding a human eye, comprising:
- a container made of a first material that defines a volume, where the volume provides a seal for containing a filler material, the container comprising a generally toroidal geometry;
- the filler material being provided within the volume defined by the container, the filler material comprising a second material different from the first material; both the first and second materials provide shielding against beta particle or low energy gamma radiation; and
- the container further defining an eye-shaped aperture through the generally toroidal geometry such that an object may pass through the eye-shaped aperture, while the container maintains its seal for the filler material, the eye-shaped aperture having a first perimeter that is equal to or greater than a second perimeter of the human eye, the container being configured to be positioned adjacent to and flexibly conform to an anatomy of an area of a human face surrounding the human eye, the generally toroidal geometry having a first width and second width, the first width being proximate to a corner of the eye-shaped aperture, the second width being proximate to a lower portion of the eye-shaped aperture, the first width being greater than the second width.

11. The system of claim 10, wherein the container further comprises at least one tab and a hole for receiving a fastener.

12. The system of claim 11, wherein the at least one tab and hole extend from the toroidal geometry.

13. The system of claim 10, wherein the first material comprises at least one of: a solid material that is a flexible and tear-resistant, and a material suitable for contact with skin.

14. The system of claim 10, wherein the second material comprises at least one of: a liquid, gel, or pliable material.

15. The system of claim 10, wherein the second material comprises at least one of: water, carbomer, carbopol, xanthan gum, gelatin, gelatinous materials, silicone, an alginate, and flexible or semi-rigid, or moldable firmer compounds.

16. The system of claim 10, wherein the toroidal geometry has a first width dimension and a second width dimension around its circumference.

17. The system of claim 10, wherein the container is for a medical procedure involving the eye.

18. The system of claim 17, wherein the aperture of the container may receive a medical instrument which has a beta particle or low energy gamma radiation source.

19. The system of claim 10, wherein the container comprises a first lobe and a second lobe, the second lobe comprising the toroidal geometry.

20. The system of claim 10, further comprising a mounting support that couples to the container.

* * * * *